United States Patent
Glacer et al.

(10) Patent No.: US 9,679,856 B2
(45) Date of Patent: Jun. 13, 2017

(54) SYSTEM AND METHOD FOR A MICROFABRICATED FRACTURE TEST STRUCTURE

(71) Applicant: Infineon Technologies AG, Neubiberg (DE)

(72) Inventors: Christoph Glacer, Munich (DE); Alfons Dehe, Reutlingen (DE); John Brueckner, Reinsdorf (DE)

(73) Assignee: Infineon Technologies AG, Neubiberg (DE)

( * ) Notice: Subject to any disclaimer, the term of this patent is extended or adjusted under 35 U.S.C. 154(b) by 529 days.

(21) Appl. No.: 14/201,260

(22) Filed: Mar. 7, 2014

(65) Prior Publication Data

US 2015/0255407 A1    Sep. 10, 2015

(51) Int. Cl.

| | |
|---|---|
| *G01R 31/26* | (2014.01) |
| *H01L 23/00* | (2006.01) |
| *G01N 3/08* | (2006.01) |
| *B81C 99/00* | (2010.01) |
| *G01N 3/02* | (2006.01) |

(52) U.S. Cl.
CPC .......... *H01L 23/564* (2013.01); *B81C 99/004* (2013.01); *G01N 3/02* (2013.01); *G01N 3/08* (2013.01); *G01N 2203/0017* (2013.01); *G01N 2203/0286* (2013.01); *G01N 2203/0298* (2013.01); *H01L 2924/0002* (2013.01)

(58) Field of Classification Search
None
See application file for complete search history.

(56) References Cited

U.S. PATENT DOCUMENTS

| | | | |
|---|---|---|---|
| 5,786,621 | A | 7/1998 | Saif et al. |
| 6,466,042 | B1 | 10/2002 | Nam |
| 6,567,715 | B1 | 5/2003 | Sinclair et al. |
| 2003/0117158 | A1 | 6/2003 | Goldbach et al. |

(Continued)

FOREIGN PATENT DOCUMENTS

| | | |
|---|---|---|
| CN | 103512508 A | 1/2014 |
| CN | 103579196 A | 2/2014 |

(Continued)

OTHER PUBLICATIONS

Fabregue et al.; "multipurpose nanomechancial testing machines revealing the size-dependent strength and high ductility of pure aluminium submicron films"; Micro & Nano Letters; Apr. 2007, pp. 13-16.*

(Continued)

*Primary Examiner* — Shaun Campbell
(74) *Attorney, Agent, or Firm* — Slater Matsil, LLP

(57) ABSTRACT

According to an embodiment, a micro-fabricated test structure includes a structure mechanically coupled between two rigid anchors and disposed above a substrate. The structure is released from the substrate and includes a test layer mechanically coupled between the two rigid anchors. The test layer includes a first region having a first cross-sectional area and a constricted region having a second cross-sectional area smaller than the first cross-sectional area. The structure also includes a first tensile stressed layer disposed on a surface of the test layer adjacent the first region.

25 Claims, 12 Drawing Sheets

(56) References Cited

U.S. PATENT DOCUMENTS

| | | | |
|---|---|---|---|
| 2010/0057381 A1* | 3/2010 | Pardoen | G01L 5/0047 |
| | | | 702/42 |
| 2010/0224006 A1* | 9/2010 | Pardoen | G01L 5/0047 |
| | | | 73/826 |
| 2014/0027772 A1 | 1/2014 | Zundel et al. | |

FOREIGN PATENT DOCUMENTS

| | | |
|---|---|---|
| DE | 10162983 A1 | 7/2003 |
| KR | 1020040002953 | 1/2004 |
| WO | 9321748 | 10/1993 |
| WO | 2007093018 A2 | 8/2007 |

OTHER PUBLICATIONS

Kamiya, S. et al., Process Temperature-Dependent Mechanical Properties of Polysilicon Measured Using a Novel Tensile Test Structure, Journal of Microelectromechanical Systems, vol., 16 No. 2, Apr. 2007, pp. 202-212.

\* cited by examiner

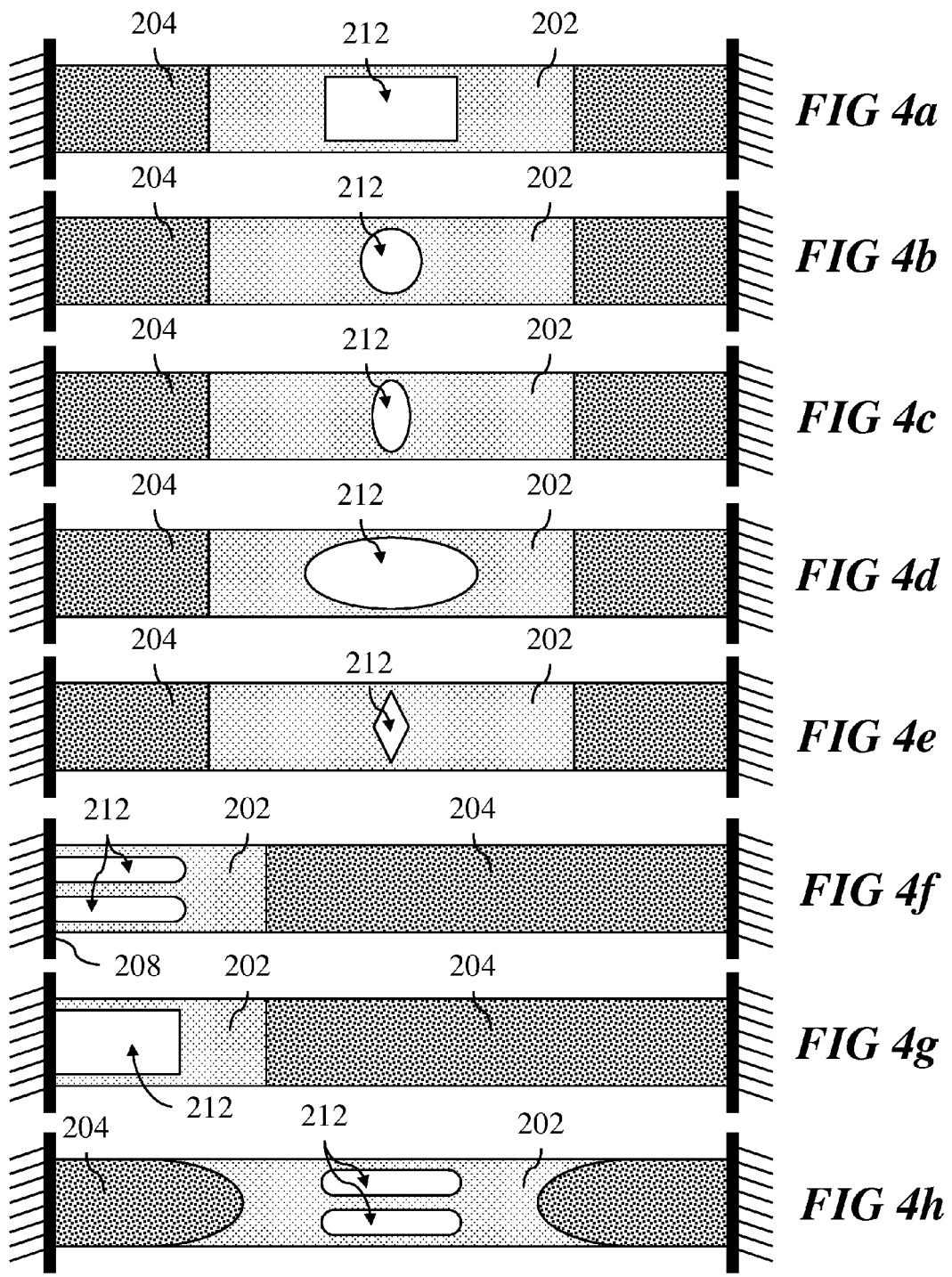

SYSTEM AND METHOD FOR A MICROFABRICATED FRACTURE TEST STRUCTURE

TECHNICAL FIELD

The present invention relates generally to micro-fabricated structures, and, in particular embodiments, to a system and method for a micro-fabricated fracture test structure.

BACKGROUND

Microfabrication is the process of fabrication of miniature structures of micrometer scales and smaller. Historically, the earliest microfabrication processes were used for integrated circuit fabrication, also known as "semiconductor manufacturing" or "semiconductor device fabrication." In addition, the fields of microelectromechanical systems (MEMS), microsystems (European terminology), micromachines (Japanese terminology) and subfields, such as microfluidics/lab-on-a-chip, optical MEMS, RF MEMS, PowerMEMS, BioMEMS, and other extensions into nanoscale dimensions (for example NEMS, for nanoelectromechanical systems) have used, adapted, or extended microfabrication methods. Flat-panel displays and solar cells also use similar techniques.

Generally, the process of microfabrication includes precisely controlled steps to form tiny structures with specific shapes or dimensions. The process of forming these tiny structures may include additive steps where materials are deposited or formed and also may include subtractive steps where materials are removed by patterning and etching or other known techniques. The fabrication of such small and varied devices presents numerous challenges in terms of, for example, process variation, quality control, and structure characterization.

One specific example topic area includes characterization. Because the fabricated devices have dimensions on the micrometer scale or less, the device performance or function may change significantly with only small variations in material or geometric properties. Further, because the processes used are applied to such tiny structures, the variation within processes may cause small variations in the material or geometric properties to be common, even for devices fabricated on a same semiconductor wafer with the same device design and, hence, the same sequence of processing steps during fabrication. Thus, for example, the same design may be applied to 100 devices on a single wafer or on different wafers, but each device has a significantly different performance due to process variations. Characterizing the fabricated devices in order to determine the actual performance may then be useful and not always easy.

One approach to characterizing fabricated devices is by using test structures. Test structures are structures fabricated on a wafer with the designed devices that may be tested during or after fabrication in order to determine material and geometric properties of the fabricated designed device.

SUMMARY OF THE INVENTION

According to an embodiment, a micro-fabricated test structure includes a structure mechanically coupled between two rigid anchors and disposed above a substrate. The structure is released from the substrate and includes a test layer mechanically coupled between the two rigid anchors. The test layer includes a first region having a first cross-sectional area and a constricted region having a second cross-sectional area smaller than the first cross-sectional area. The structure also includes a first tensile stressed layer disposed on a surface of the test layer adjacent the first region.

BRIEF DESCRIPTION OF THE DRAWINGS

For a more complete understanding of the present invention, and the advantages thereof, reference is now made to the following descriptions taken in conjunction with the accompanying drawings, in which:

FIGS. 4a-4h illustrate top views of various embodiment test structures;

Corresponding numerals and symbols in the different figures generally refer to corresponding parts unless otherwise indicated. The figures are drawn to clearly illustrate the relevant aspects of the embodiments and are not necessarily drawn to scale.

DETAILED DESCRIPTION OF ILLUSTRATIVE EMBODIMENTS

The making and using of various embodiments are discussed in detail below. It should be appreciated, however, that the various embodiments described herein are applicable in a wide variety of specific contexts. The specific embodiments discussed are merely illustrative of specific ways to make and use various embodiments, and should not be construed in a limited scope.

Description is made with respect to various embodiments in a specific context, namely fabricated test structures, and more particularly, test structures for determining the fracture strength of thin films. Some of the various embodiments described herein include microelectromechanical systems (MEMS) fabrication, integrated circuit (IC) fabrication, thin film test structures, fabrication of thin film test structures, and test structures for determining the fracture strength of a thin film. In other embodiments, aspects may also be applied to other applications involving any type of test structure according to any fashion as known in the art.

According to various embodiments described herein, fabricated thin films or layers may have varying thickness and material properties. As a result of these variations, the fracture strength of the layer or thin film may also vary significantly. In various embodiments, test structures are disclosed herein that may be used to determine the fracture strength of a thin film or layer during or after fabrication. These test structures include a plurality of structures having various tensile stresses applied to each structure. A subset of the plurality of structures is designed to fracture during a fabrication sequence. Inspection of the test structures and determination of the subset that fracture is used to determine the fracture strength of the thin film or layer under test.

Figure 1:
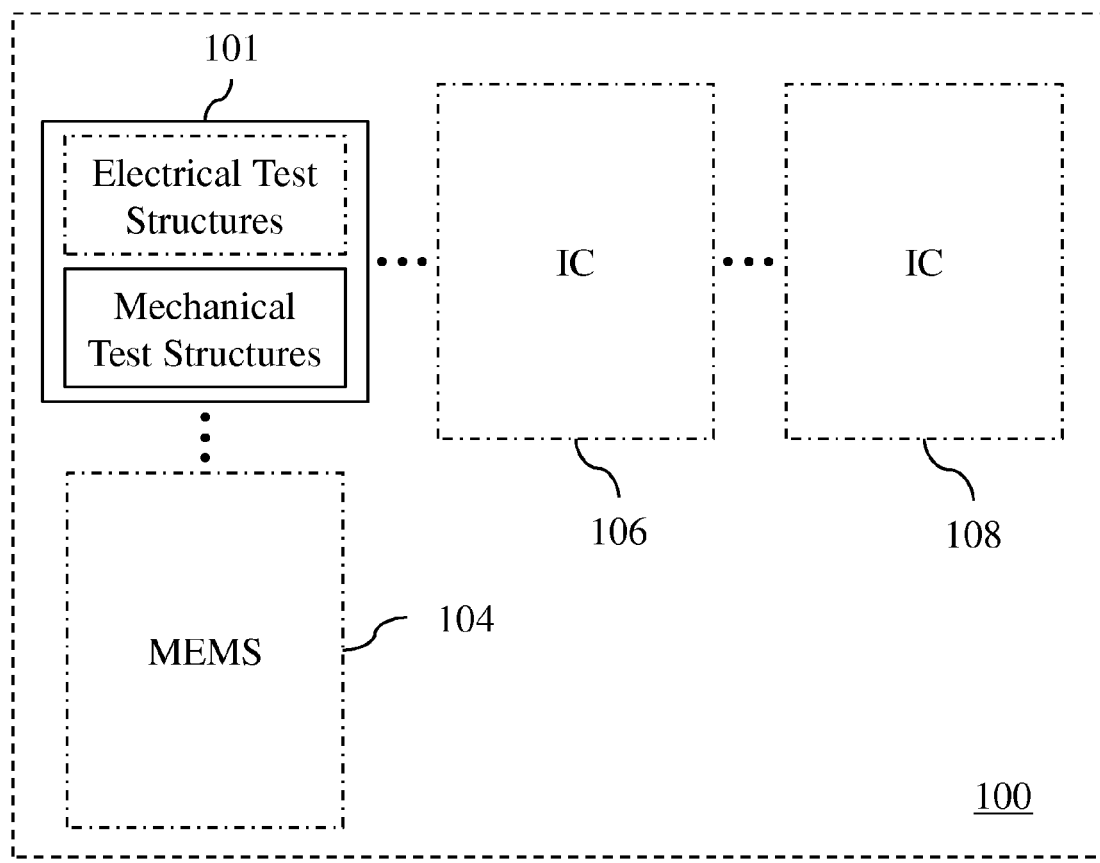
FIG. 1 illustrates a block diagram of a fabricated system employing an embodiment test structure.

FIG. 1 illustrates a block diagram of a fabricated system 100 employing an embodiment test structure 101. According to various embodiments, fabricated system 100 may be referred to as wafer 100 and may include numerous components on a fabricated wafer such as MEMS 104, integrated circuit (IC) 106, and IC 108, for example. Wafer 100 may include additional MEMS and ICs or fewer MEMS or ICs. As shown, test structure 101 is fabricated on wafer 100. In some embodiments, test structure 101 is fabricated adjacent to a MEMS or IC that is being tested, such as MEMS 104, IC 106, and IC 108. In further embodiments, test structure 101 is only used to test an immediately adjacent MEMS or IC.

According to various embodiments, wafer 100 may be fabricated using any type of fabrication process that may involve, for example, many steps including any type of layer formation, such as growth or deposition, and any type of patterning of the layers, generally performed on some type of substrate. The fabrication steps discussed herein are in no way limiting as embodiment test structures may be used with any fabrication step or process as is known in the art. As briefly discussed above, fabrication processes, and particularly microfabrication processes (even nanofabrication processes), are filled with variations despite being highly controlled. The scale of the structures causes small variations in geometry on the order to micrometers, nanometers, or even smaller to affect overall performance of a fabricated device. Additionally, material properties of the fabricated structures are subject to variation as well and small variations of a material property may also affect the overall performance of the fabricated device.

For at least these reasons, embodiment test structures 101 are fabricated on wafer 100 in order to characterize the fabricated structure. As is known in the art, many types of test structures exist and may be fabricated on wafer 100 and included in test structure 101. Embodiments described herein include a tensile stress test structure for testing the fracture strength of a thin film or fabricated layer. Test structure 101 may also include optional electrical test structures for testing various electrical properties such as resistance of different materials, for example.

In addition to a general need for characterization following fabrication, determining the fracture strength may be particularly beneficial in some embodiments. For example, in a MEMS microphone common in many mobile applications such as personal computers, cell phones, and tablets, a deflectable membrane is at the center of the MEMS device. The deflectable membrane is a type of thin film that is generally released to deflect in response to incident sound pressure waves entering the microphone. The robustness of the microphone is often determined by the characteristics of the deflectable membrane. For example, the fracture strength of a thin film or layer may be determined in order to characterize a device such as a MEMS microphone.

Figure 2A:
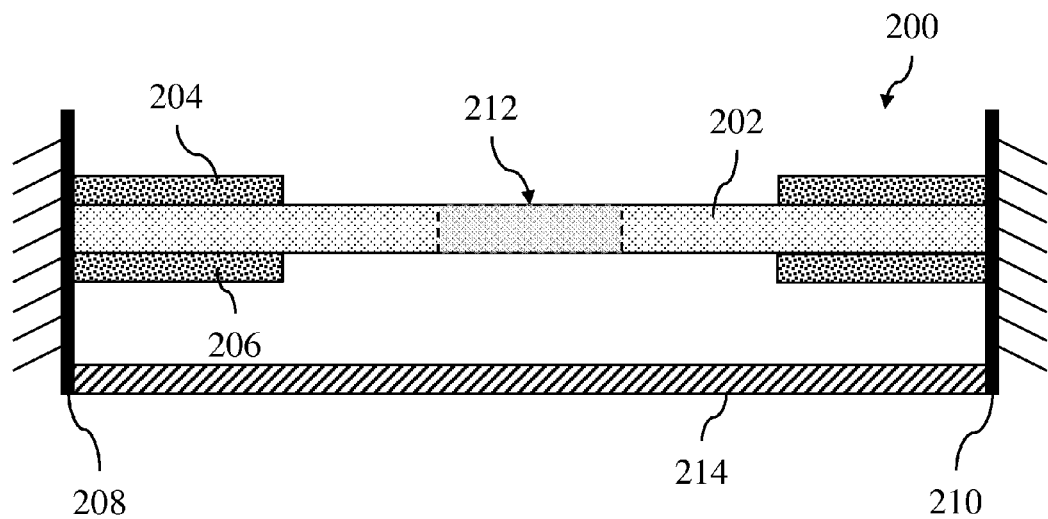
FIGS. 2a and 2b illustrate a cross-sectional view and a top view, respectively, of an embodiment test structure.
Figure 2B:
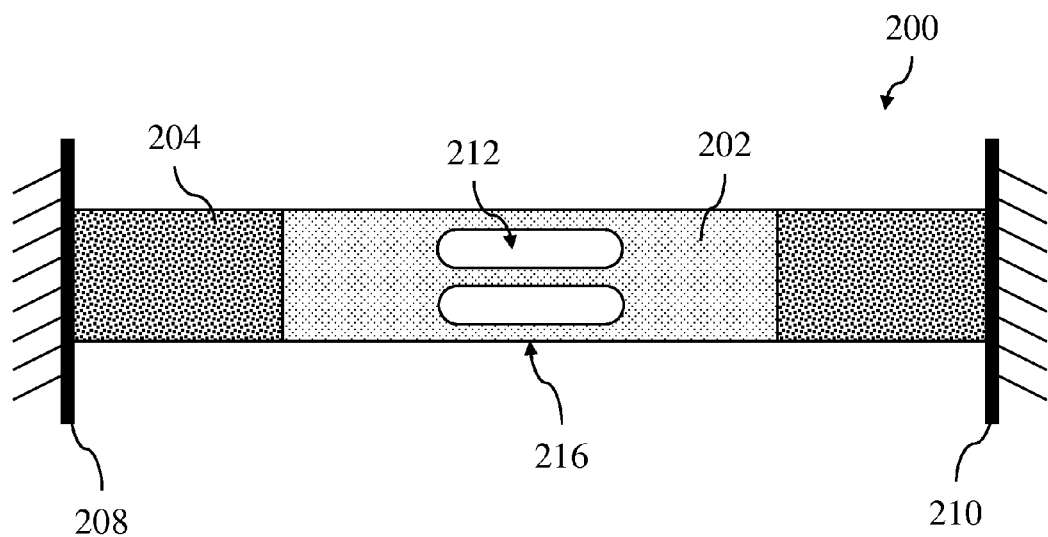

FIGS. 2a and 2b illustrate a cross-sectional view and a top view, respectively, of an embodiment test structure 200. According to various embodiments, test structure 200 includes thin film 202, top tensile film 204, and bottom tensile film 206. Thin film 202 is attached between rigid anchors 208 and 210 and has a cutout 212 at some point in the thin film 202. In various embodiments, thin film 202 is fabricated using a same fabrication process as a specific thin film of a device, such as MEMS 104 in FIG. 1, and may be fabricated adjacent to the device on a wafer. Thus, thin film 202 has similar properties and process variation as the particular thin film under test in a fabricated device. In some embodiments, electrode 214 may be formed below thin film 202 and may be configured to apply a voltage to thin film 202. Electrode 214 may be a doped region in a substrate (not shown), a metal layer, or a polysilicon layer formed on the substrate, for example.

According to various embodiments, cutout 212 produces a constricted region 216 in thin film 202. Top and bottom tensile films 204 and 206 apply a tensile stress on thin film 202. In some embodiments, the tensile stress applied by tensile films 204 and 206 causes thin film 202 to fracture in constricted region 216. In various embodiments, test structure 101 in FIG. 1 includes multiple implementations of test structure 200 in FIG. 2 with different tensile stresses applied to thin film 202 or different constricted regions 216 as will be discussed below. In such embodiments, the fracture strength of the thin film under test may be determined by inspection of the plurality of test structures and identification of which test structures fractured.

Figure 3:
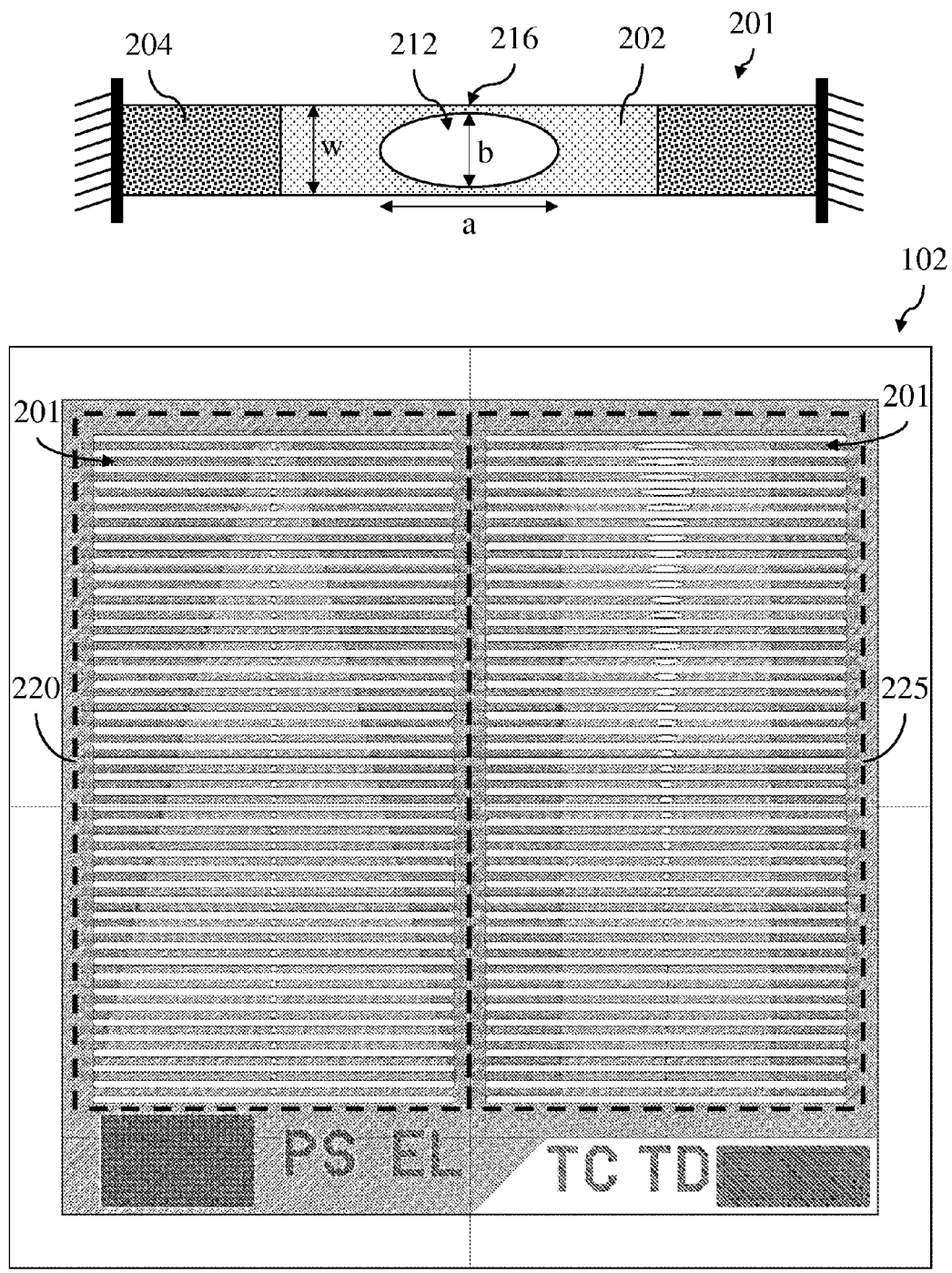
FIG. 3 illustrates a layout view of an embodiment test structure including a first group of test structures and a second group of test structures.

FIG. 3 illustrates a layout view of embodiment test structure 102 including a first group of test structures 220 and a second group of test structures 225. According to various embodiments, each group of test structures 220 and 225 includes individual test structures 201 as shown above test structure 102. Test structure 201 includes cutout 212 in thin film 202 having an elliptical shape with a long diameter (transverse diameter) a and a short diameter (conjugate diameter) b. In various embodiments, test structure 101 in FIG. 1 may include a single test structure 102 or multiple test structures 102.

According to various embodiments, the stress at which thin film 202 in test structure 201 fractures depends on the size and shape of constricted region 216, which is defined by cutout 212. Further, the tensile stress applied is determined by the amount of tensile films 204 and 206 that is applied. Based on these concepts, the groups of test structures 220 and 225 are selected to fracture some test structures 201 of the plurality and not to fracture others. The first group of test structures 220 includes test structures 201 with long diameter a and short diameter b both equal and constant throughout all test structure 201 in group 220. However, each test structure 201 in group 220 has a different amount of tensile film 204 formed on thin film 202. In various embodiments, tensile film 206 may also be formed in different amounts, or tensile film 206 may be omitted in some embodiments.

For example, the top test structure 201 in group 220 may have 90% of thin film 202 covered by tensile film 204 (or tensile film 206, inclusive), as shown. The percentage covering each test structure may be decreased moving downwards such that the bottom test structure 201 may have 2% of thin film 202 covered by tensile film 204 (or tensile film 206, inclusive), as shown. In this case, the tensile stress applied to each test structure 201 in group 220 ranges from a maximum for the top test structure to a minimum for the bottom test structure. The calculation of the tensile stress applied to each structure may be routinely performed by those skilled in the art using numerical approximations or more accurate finite element analysis with commercially available or custom software.

According to various embodiments, the second group of test structures 225 includes test structures 201 with short diameter b being constant and long diameter a ranging from top test structure to bottom test structure. In this embodiment, tensile film 204 is formed in an equal amount on thin film for each test structure 201 of group 225. Thus, group 225 includes an embodiment where the tensile stress applied to thin film 202 in each test structure 201 is constant while the stress at which the thin film 202 will fracture is not constant. As discussed above, the tensile film 206 may also be applied in an equal amount to the bottom of thin film 202 for each test structure 201 in group 225. In other embodiments, either tensile film 204 or 206 may be omitted as desired.

For example, every test structure 201 in group 225 may have 50% of thin film 202 covered with tensile film 204 (or tensile film 206, inclusive). Thus, a constant tensile stress is applied to each test structure 201 in group 225. The strength of each test structure 201 ranges as determined by the size of constricted region 216 in each test structure 201. The size of constricted region 216 is determined by long diameter a in test structure 201, which varies from a maximum in the top test structure 201 to a minimum in the bottom test structure 201 of group 225. Thus, the top test structure 201 in group 225 is more likely to fracture than the bottom test structure 201 because constricted region 216 in the top structure is longer, making the total beam formed by thin film 202 weaker. In group 225, short diameter b is held constant.

According to various embodiments, long diameter a and short diameter b are both 8 μm and the width w of the beam formed by thin film 202 is 10 μm for each test structure 201 in group 220. For test structures 201 in group 225, short diameter b is 8 μm and width w is 10 μm while long diameter a ranges from 0 μm to 100 μm. In other embodiments, each dimension may take on any value and may vary or be held constant. Further, any combination of constant and ranging dimensions may be used in various embodiments. In further particular embodiments, width w may range from 5 μm to 100 μm and short diameter b may range from 1 μm to 100 μm. The total beam length, formed by thin film 202 coupled between anchors 208 and 210, may range from 100 μm to 500 μm in some embodiments. In other embodiments, the beam length may be shorter than 100 μm or longer than 500 μm. In a particular embodiment, the beam length may be 400 μm. Additionally, the percentage of thin film 202 that is covered by tensile film 204 (or tensile film 206, inclusive) may be any percentage. Further, the shape of the cutout may take any form and produce numerous types of constricted regions, as well be explained in reference to FIGS. 4a-4h.

In further embodiments, the inventive concepts described herein are also applicable to nanoscale structures. Although the example dimensions have been primarily given in reference to MEMS, test structure 200 as a part of test structure 102 may be applied to nanoscale structures according to the same concepts. In such embodiments, the dimensions may be decreased while the same principles of applying tensile stress to thin films may still be applied.

FIGS. 4a-4h illustrate top views of various embodiment test structures as described in reference to test structure 200 and 201 with various different features. FIG. 4a illustrates a test structure with a rectangular cutout 212. FIG. 4b illustrates a test structure with a circular cutout 212. FIG. 4c illustrates a test structure with an elliptical cutout 212 having a larger vertical diameter. FIG. 4d illustrates a test structure with an elliptical cutout 212 having a larger horizontal diameter. FIG. 4e illustrates a test structure with a diamond shaped cutout 212. FIG. 4f illustrates a test structure with cutouts 212 near anchor 208 and tensile film 204 on the right side of thin film 202. FIG. 4g illustrates a test structure with a rectangular cutout 212 near anchor 208 and tensile film 204 on the right side of thin film 202. FIG. 4h illustrates a test structure with cutouts 212 and tensile film 204 patterned with a non-square pattern. Each test structure in FIGS. 4a-4h may be formed and used as described in reference to FIGS. 2 and 3 above. For example, every test structure in FIGS. 4a-4h may include tensile film 206 on a bottom surface of thin film 202. In the various embodiments, tensile film 206 may be patterned to match tensile film 204 or may be patterned differently.

Figure 5A:
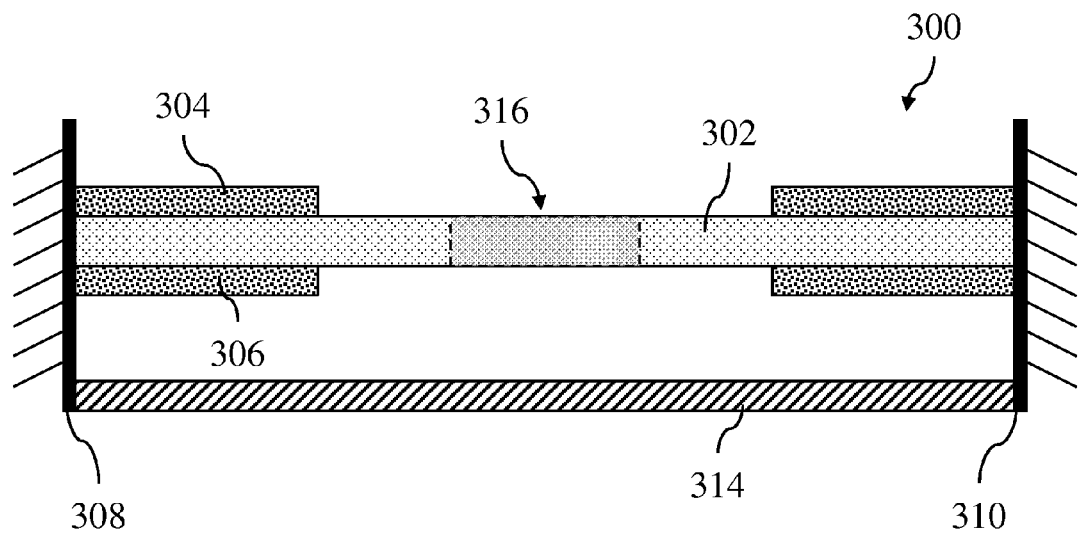
FIGS. 5a and 5b illustrate a cross-sectional view and a top view, respectively, of a further embodiment test structure.
Figure 5B:
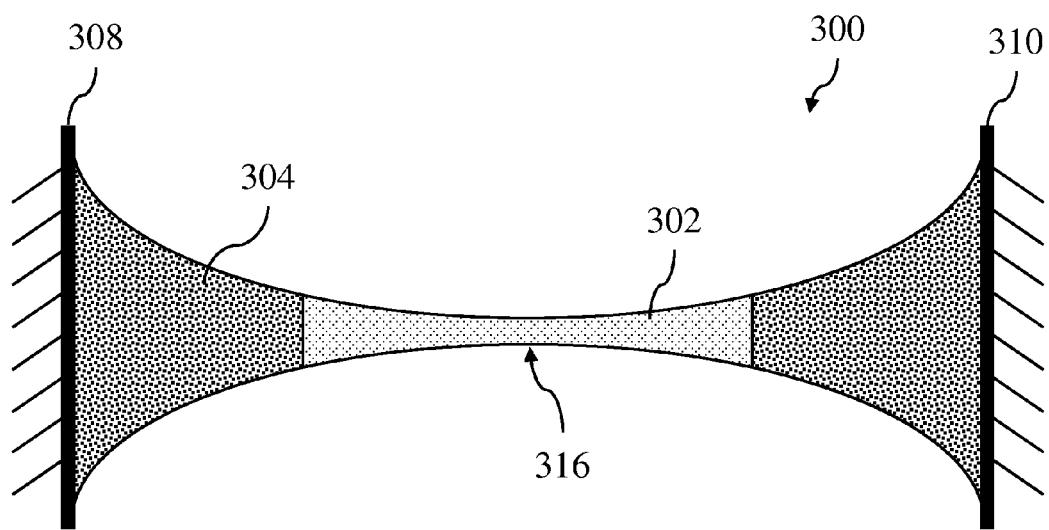

FIGS. 5a and 5b illustrate a cross-sectional view and a top view, respectively, of a further embodiment test structure 300. According to various embodiments, test structure 300 includes thin film 302 with tensile films 304, above, and 306, below. In the various embodiments, either tensile film 304 or 306 may be omitted and only a single tensile film 304 or 306 may be used. Thin film 302 also includes a constricted region 316. As shown in FIG. 5b, constricted region 316 is a narrowed region that is more prone to fracture, in some embodiments. Thin film 302 is formed between rigid anchors 308 and 310. Test structure 300 may also include electrode 314 for applying an additional force in order to deflect the fixed-fixed bean formed by thin film 302. Test structure 300 differs from test structure 200 and the various embodiments discussed in FIGS. 4a-4h in the shape of the beam. Test structure 300 is formed of a tapered beam, generally without cutout regions. In other embodiments, elements of all the embodiments may be freely interchanged, such as the tapering of test structure 300 and the cutouts of test structure 200, for example.

Just as with the other test structures described herein, the tensile force applied to thin film 302 is related to the amount of tensile film 304 and 306 applied. The larger the area of overlap, as seen from the top view in FIG. 5b, the larger the tensile force applied to thin film 302. Further, the longer the beam and the narrower the constricted region, the lower the force required to fracture or rupture thin film 302.

Figure 6:
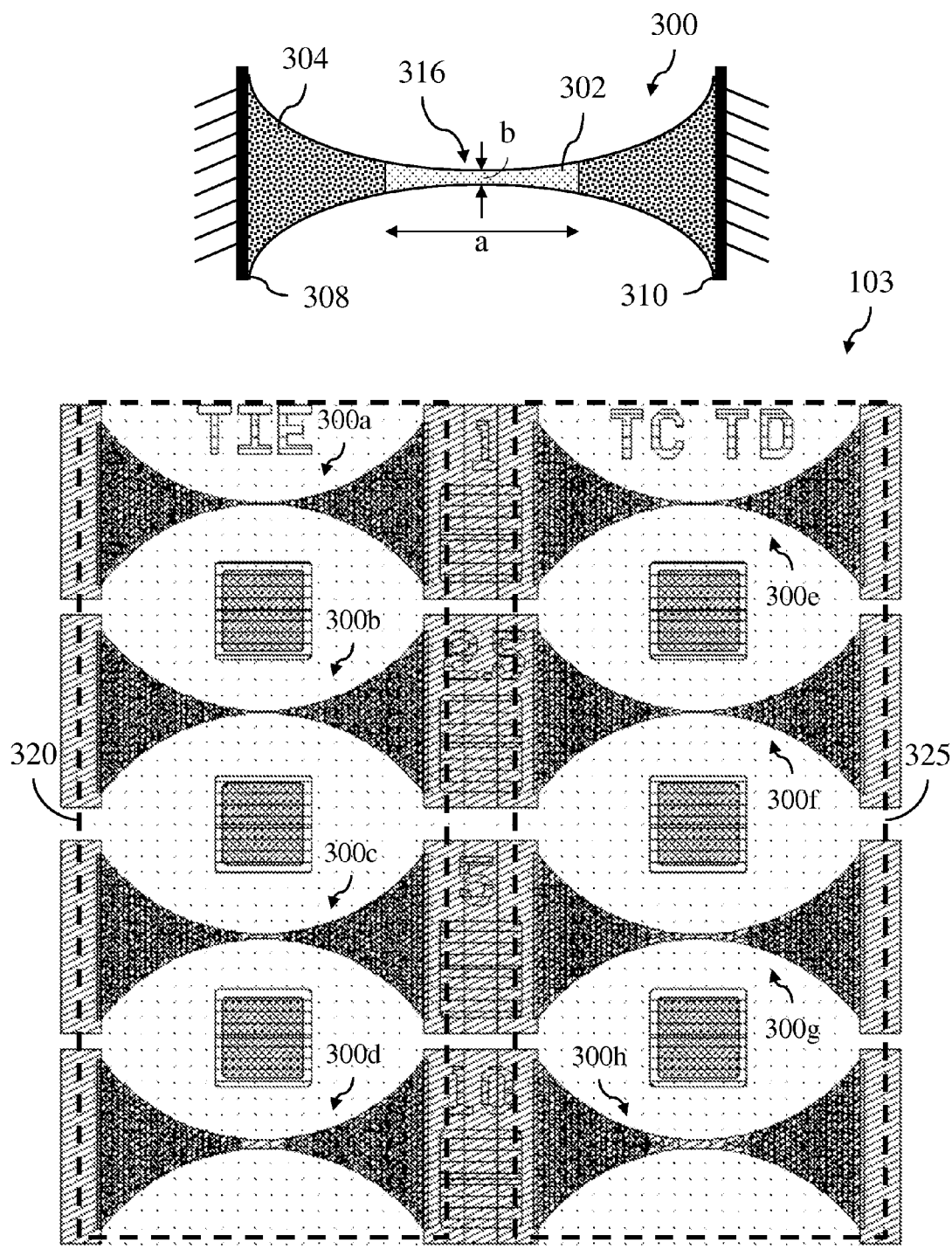
FIG. 6 illustrates a layout view of a further embodiment test structure including a first group of test structures and a second group of test structures.

FIG. 6 illustrates a layout view of embodiment test structure 103 including a first group of test structures 320 and a second group of test structures 325. According to various embodiments, each group of test structures 320 and 325 includes individual test structures 300 as shown above test structure 103. Test structure 103 includes constricted region 316 in thin film 302, which is tapered from wider regions at rigid anchors 308 and 310. The length of uncovered thin film 302 is given by length a and the width of the beam formed by thin film 302 is given by width b. In various embodiments, test structure 101 in FIG. 1 may include a single test structure 103, multiple test structures 103, or some combination of test structures 102 as described in reference to FIG. 3 and test structures 103.

As discussed above, the stress at which thin film 302 in test structure 300 fractures depends on the size and shape of constricted region 316, which is generally defined for the embodiments shown in FIGS. 5-7 by length a and width b. Further, the tensile stress applied to the beam formed by thin film 302 is determined by the amount of tensile films 304 and 306 that is applied.

Based on the above concepts, the groups of test structures 320 and 325 are selected to fracture some test structures 300a-300h of the plurality and not to fracture others. The first group of test structures 320 includes test structures 300a-300d with a constant first length a and with a width b that increases moving downwards in FIG. 6. For example, the length a of each beam in group 320 may be 54 µm while the width b of test structure 300*a* is 1 µm, the width b of test structure 300*b* is 2.5 µm, the width b of test structure 300*c* is 5 µm, and the width b of test structure 300*d* is 10 µm. The second group of test structures 325 includes test structures 300*e*-300*h* with a constant first length a and with a width b that increases moving downwards in FIG. 6. For example, the length a of each beam in group 325 may be 122 µm while the width b of test structure 300*e*-330*h* mimics that of test structures 300*a*-300*d* in group 320, respectively. In various embodiments, length a and width b may each be set to any value and may be varied separately or together in different test structures.

According to various embodiments, any number of test structures 300 may be used of any dimension. For example, length a may range from 10 µm to 1000 µm and width b may range from 0.1 µm to 100 µm. Other dimensions may also be used. As mentioned above, nanoscale structures based on these same concepts are also envisioned. In such embodiments, the structures will be formed with nanoscale widths b and lengths a in addition to other scaling related modifications.

Figure 7A:
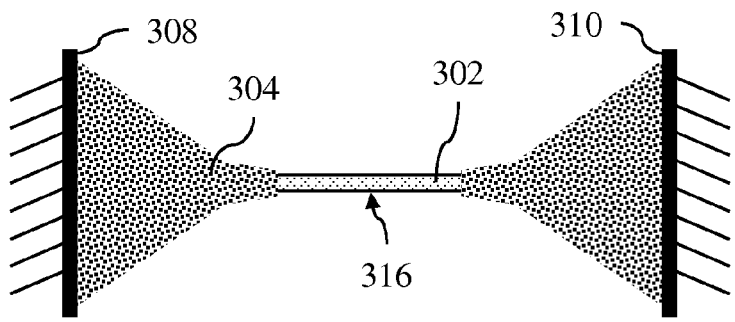
FIGS. 7a-7e illustrate top views of various further embodiment test structures.
Figure 7B:
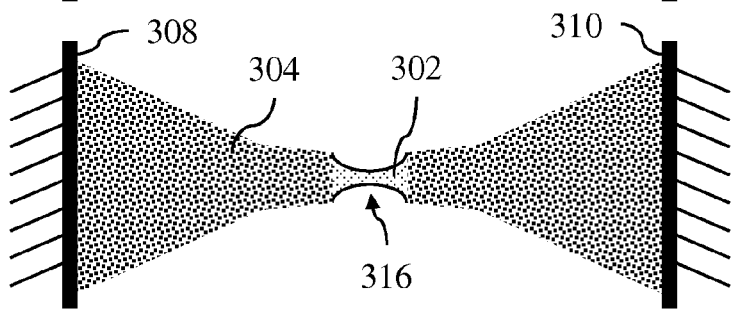
Figure 7C:
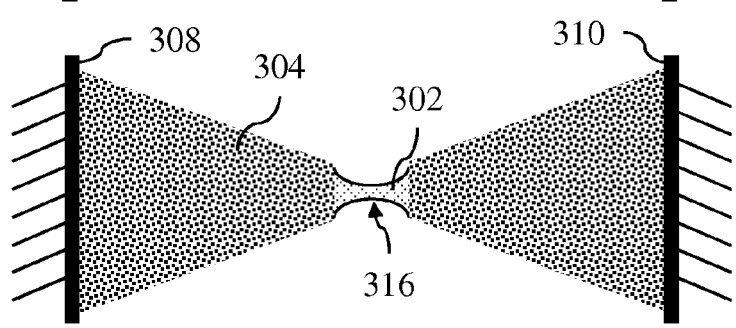
Figure 7D:
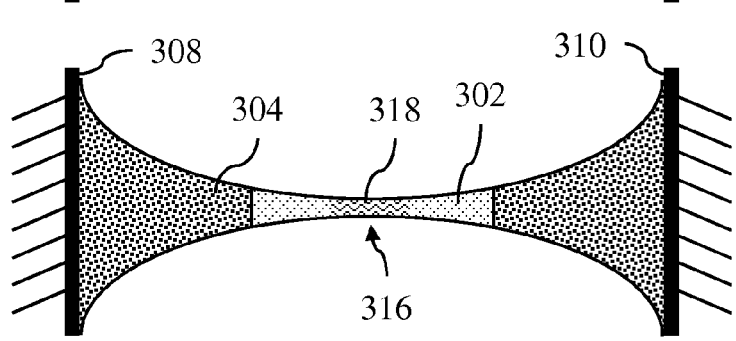
Figure 7E:
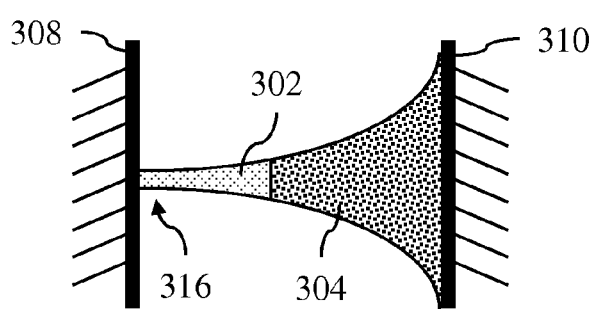

FIGS. 7*a*-7*e* illustrate top views of various embodiment test structures as described in reference to test structure 300 with various different features. FIG. 7*a* illustrates a test structure with a two-step linearly tapered region feeding into a constant width constricted region. FIG. 7*b* illustrates a test structure with a different two step linearly tapered region feeding into a further curved tapered constricted region. FIG. 7*c* illustrates a test structure with a single step linearly tapered region feeding into a further curved tapered constricted region. FIG. 7*d* illustrates a test structure with a curved tapered region throughout as shown in FIGS. 5*a* and 5*b*, except constricted region 316 includes corrugation 318. FIG. 7*e* illustrates a test structure with a curved tapered region throughout, except that constricted region 316 is coupled directly to anchor 308.

Each test structure in FIGS. 7*a*-7*e* may be formed and used as described in reference to the other figures. For example, every test structure in FIGS. 7*a*-7*h* may include tensile film 306 on a bottom surface of thin film 302. In the various embodiments, tensile film 306 may be patterned to match tensile film 304 or may be patterned differently.

Figure 8A:
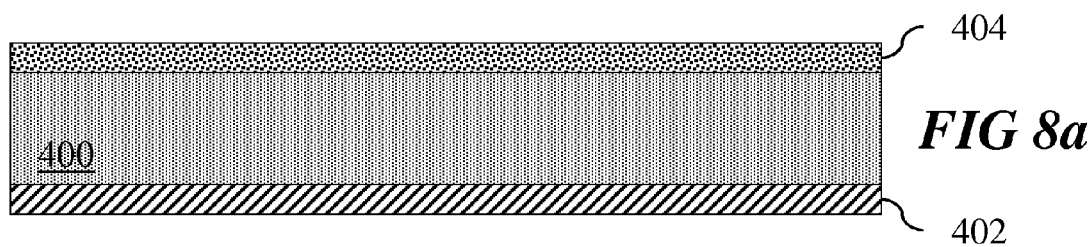
FIGS. 8a-8h illustrate an embodiment fabrication sequence for an embodiment test structure.

FIGS. 8*a*-8*h* illustrate an embodiment fabrication sequence for an embodiment test structure according to any of the embodiments described herein. FIG. 8*a* illustrates a structure with an electrode layer 402 that may be a doped part of a substrate (not shown), such as a silicon substrate. In various embodiments, the substrate may be any material and electrode layer 402 may also be a metal layer deposited on the substrate. A sacrificial layer 400 is deposited on top of electrode layer 402. In various embodiments, sacrificial layer 400 may be formed of any type of material, such as silicon dioxide, a thermal oxide, carbon, tetraethyl orthosilicate (TEOS), or others, for example. Tensile layer 404 is deposited on sacrificial layer 400. In various embodiments, tensile layer 404 may be formed of any material that applies a tensile force when released, such as silicon nitride or aluminum oxide, for example.

According to various embodiments, tensile layer 404 may be any thickness. In some particular embodiments, tensile layer 404 is between 50 nm and 1 µm thick, and particularly about 200 nm in one embodiment. According to various embodiments, sacrificial layer 400 is much thicker than tensile layer 404, such as at least 10 times as thick, for example. In alternative embodiments, sacrificial layer 400 may any thickness regardless of the thickness of tensile layer 404.

Figure 8B:
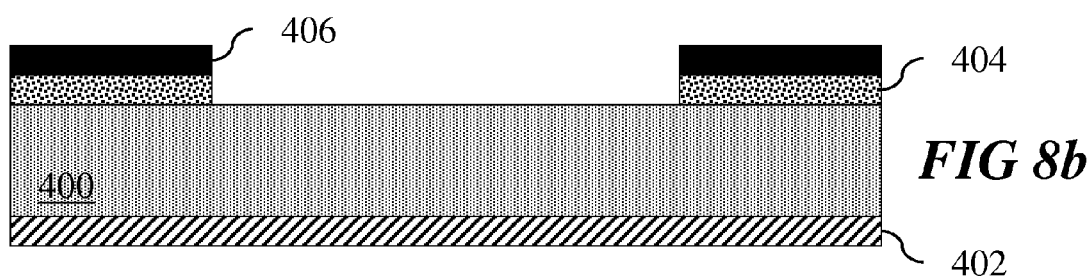

FIG. 8*b* illustrates a structure after photoresist layer 406 is applied and patterned according to a first mask pattern and an etch process is performed on tensile layer 404. Thus, FIG. 8*b* shows tensile layer 404 patterned according to the first mask pattern.

Figure 8C:
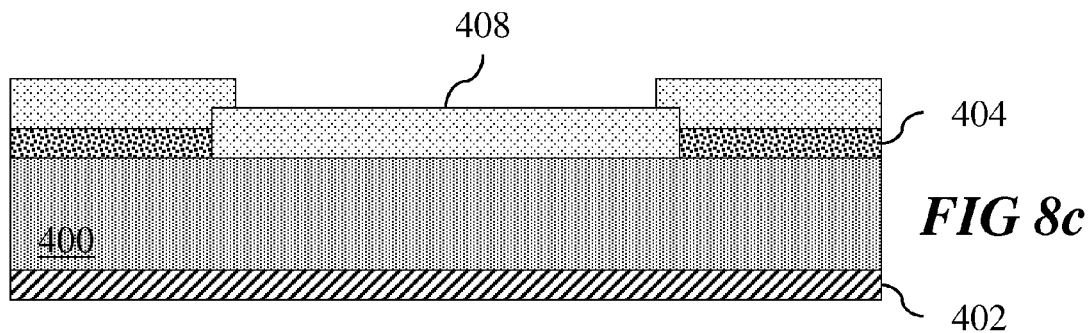

FIG. 8*c* illustrates a structure after a thin film 408 is deposited on patterned tensile layer 404. In various embodiments, thin film 408 may form a contour matching the patterning of tensile layer 404. In other embodiments, additional sacrificial layer material, or another material, may be deposited and the structure may undergo a chemical mechanical polish (CMP), or equivalent, to planarize the structure before thin film 408 is deposited. According to various embodiments, thin film 408 may be formed of any type of material, such as silicon, polysilicon, oxide, any semiconductor material, or a combination of such layers. In other embodiments, thin film 408 may be formed of a polymer or a metal. Thin film 408 may be any thickness as described in reference to tensile layer 404, such as about 200 nm, for example.

Figure 8D:
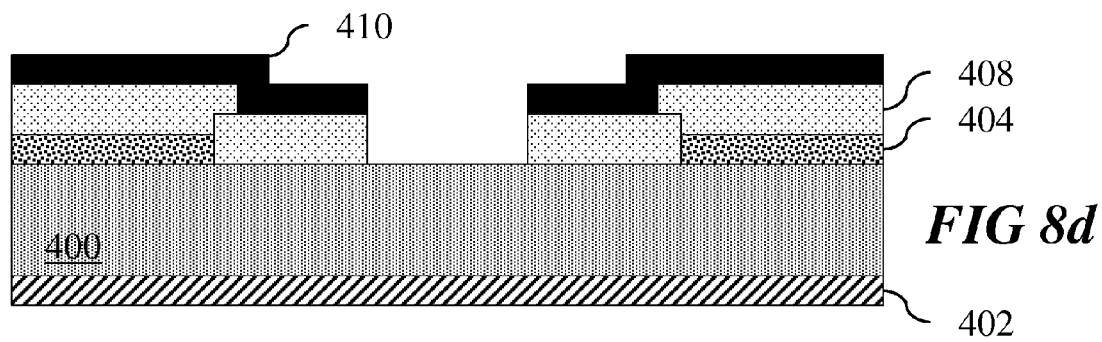

FIG. 8*d* illustrates a structure after photoresist layer 410 is applied and patterned according to a second mask pattern and a further etch process is performed on thin film 408. Thus, FIG. 8*d* shows thin film 408 patterned according to the second mask pattern.

Figure 8E:
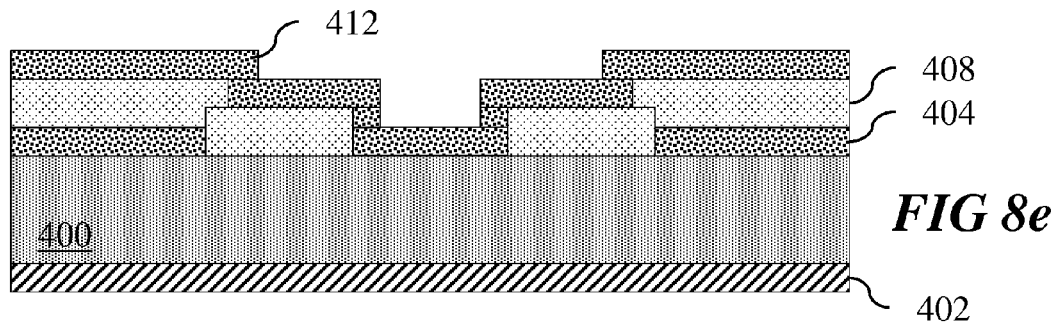

FIG. 8*e* illustrates a structure after tensile layer 412 is deposited on patterned thin film 408 and patterned tensile layer 404. Again, tensile layer 412 may follow the contour of thin film 408. In other embodiments, the structure may be planarized as described above before tensile layer 412 is deposited. Tensile layer 412 may be formed of any material and of any thickness as described in reference to tensile layer 404 above.

Figure 8F:
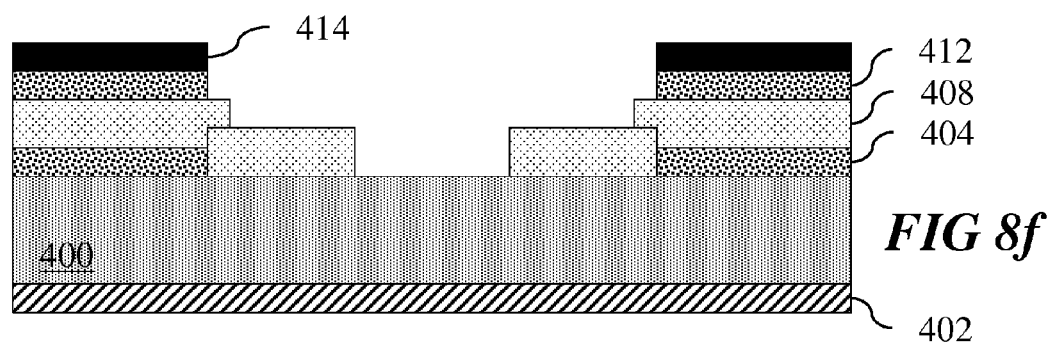

FIG. 8*f* illustrates a structure after photoresist layer 414 is applied and patterned according to a third mask pattern and another etch process is performed on tensile layer 412. Thus, FIG. 8*f* shows tensile layer 412 patterned according to the third mask pattern.

Figure 8G:
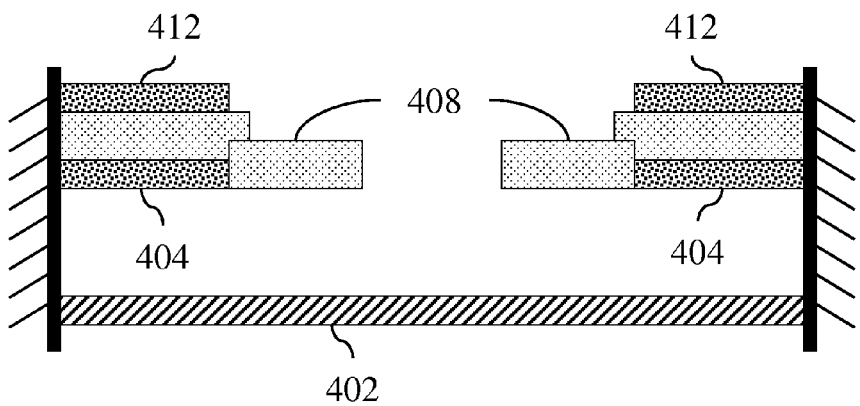
Figure 8H:
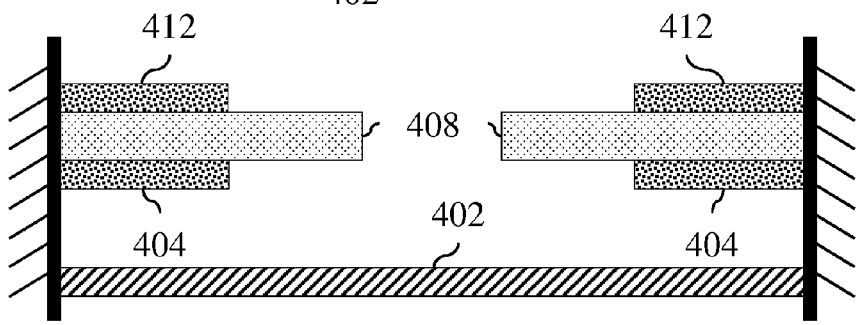

FIGS. 8*g* and 8*h* illustrate cross sectional views of completed test structures after photoresist 414 is removed and sacrificial layer 400 is removed in a release step. FIG. 8*g* illustrates a structure that was not planarized during fabrication and FIG. 8*h* illustrates a structure that was planarized during fabrication between layer depositions, as mentioned above. As described in reference to the other figures, some of the structures may fracture after the sacrificial layer is removed and the thin film is released. In various embodiments, the tensile layers operate to apply a tensile stress on the order of 1 GPa. The cross section is taken at a point where a cutout is patterned as described in FIGS. 2-4, but the same general fabrication steps may be applied to form any of the structures discussed herein or equivalents. Further, one of ordinary skill in the art will recognize that the various steps described herein may be modified to form an equivalent structure and such modifications are with the scope of this disclosure.

Figure 9:
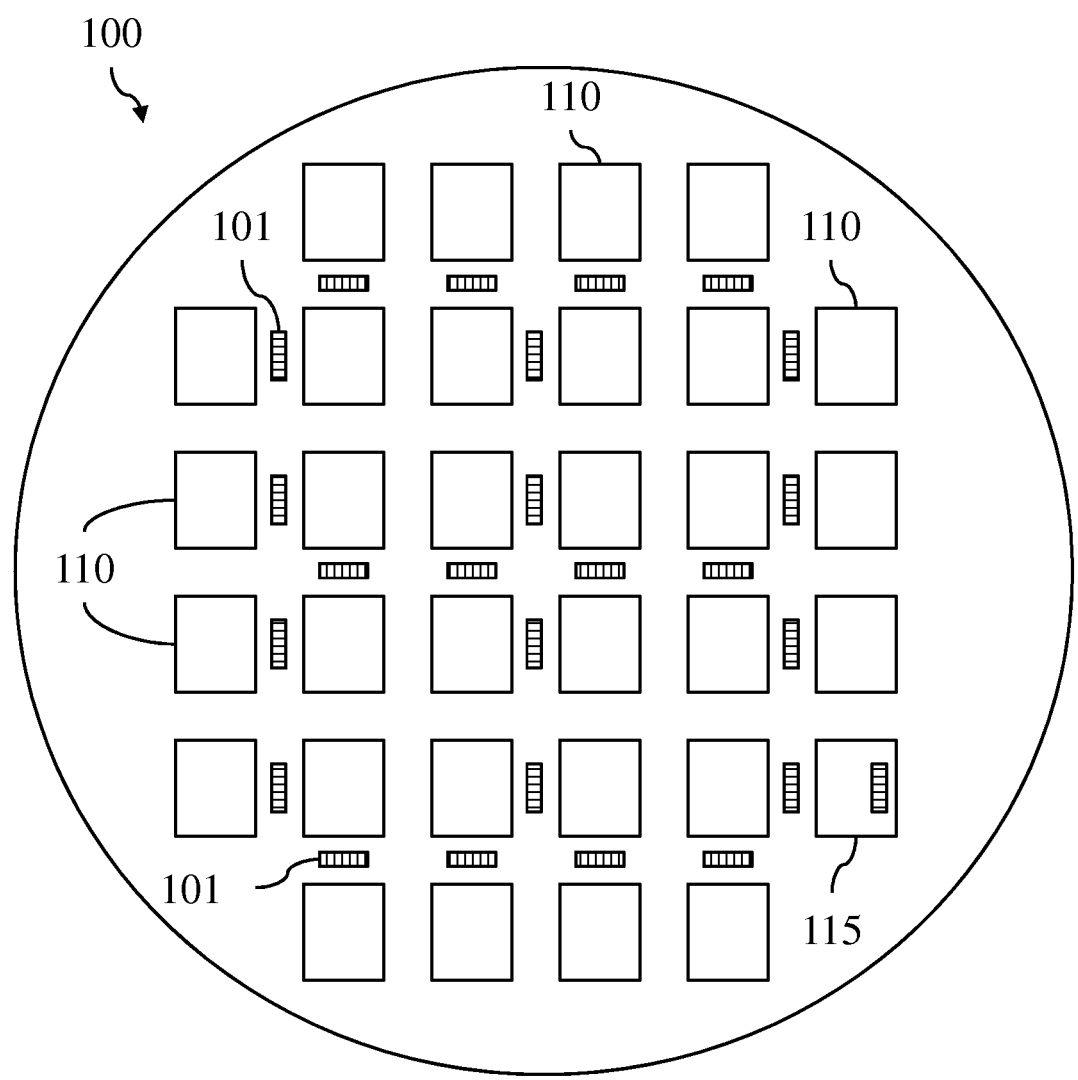
FIG. 9 illustrates a top view of a semiconductor wafer including embodiment test structures.

FIG. 9 illustrates an additional top view of semiconductor wafer 100 including embodiment test structures 101 and functional blocks 110. According to various embodiments, test structure 101 may include test structure sets 102 and 103 as described in reference to the other figures, as well as other test structures, mechanical or electrical in nature. Test structures 101 may be distributed throughout semiconductor wafer 100 as shown, or in any other arrangement. Functional block 110 may include mechanical structures such as MEMS, integrated circuits, or a combination thereof. Functional block 115 is a functional block similar to functional block 110 except that test structure 101 is included within the functional block. In various embodiments, the functional blocks are the individual dies that will be singulated in a dicing process. Thus, functional block 115 includes test structures 101 that may be part of the die.

Figure 10:
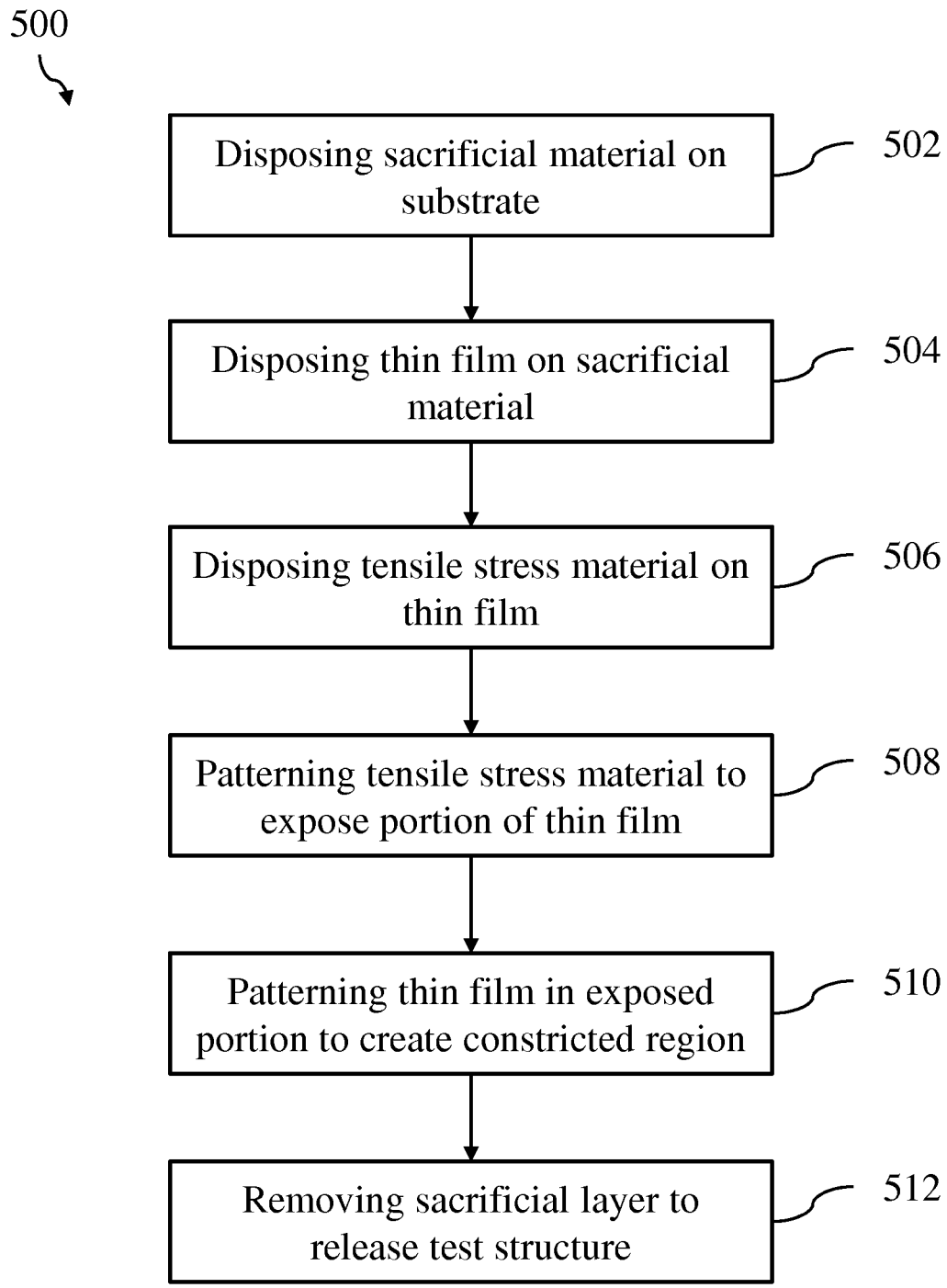
FIG. 10 illustrates a flowchart diagram of a further embodiment fabrication sequence.

FIG. 10 illustrates a flowchart diagram of a further embodiment fabrication sequence 500 for producing an embodiment test structure including steps 502-512. According to various embodiments, step 502 includes disposing a sacrificial material on a substrate, step 504 includes disposing a thin film on the sacrificial material, and step 506 includes disposing a tensile stress material on the thin film. Step 508 includes patterning the tensile stress material to expose a portion of the thin film and step 510 includes patterning the thin film in the exposed portion to create a constricted region. Finally, step 512 includes removing the sacrificial material to release the test structure.

According to various embodiments, fabrication sequence 500 may be modified according to another order of process steps and may further include other processing steps. Particularly, fabrication sequence 500 may be modified according to any of the principles described in reference to FIGS. 8*a*-8*h*. For example, an additional tensile stress material may be disposed below the thin film, an electrode may be formed in a substrate, and additional patterning steps may be performed in any order.

Figure 11:
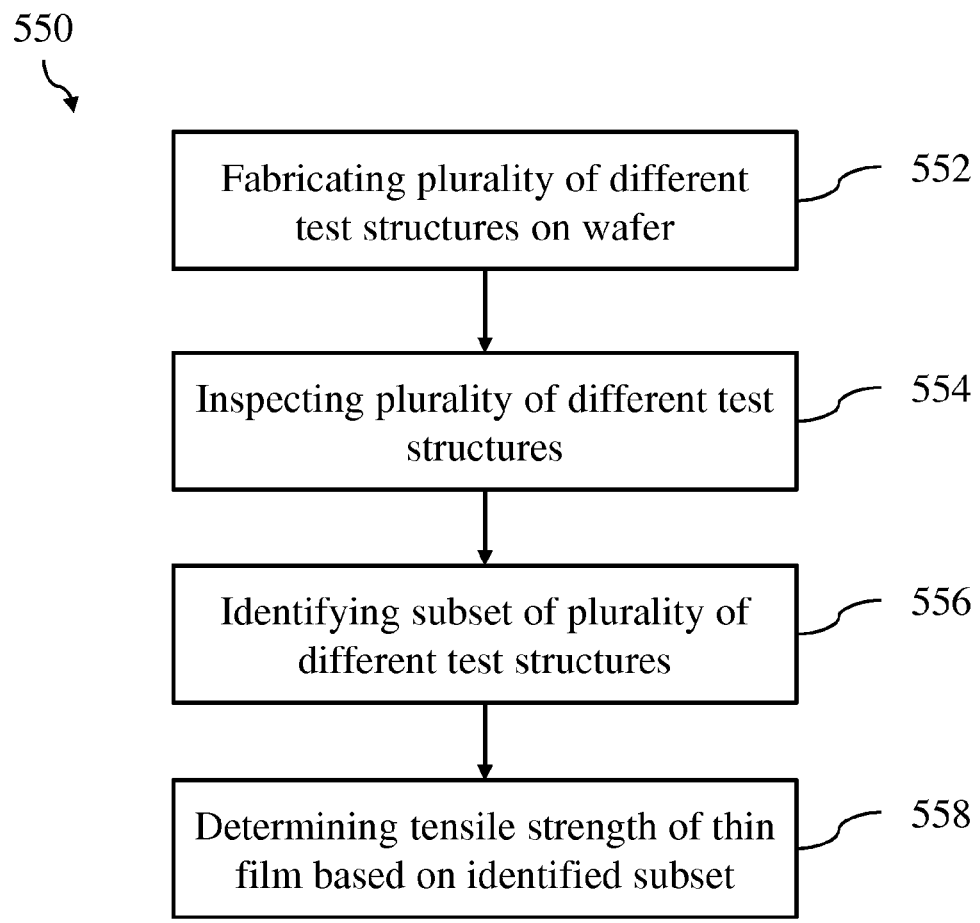
FIG. 11 illustrates a flowchart diagram of an embodiment method of using an embodiment test structure to determine the tensile strength of a thin film.

FIG. 11 illustrates a flowchart diagram of an embodiment method 550 of determining the tensile strength of a thin film using an embodiment test structure including steps 552-558. According to various embodiments, step 552 includes fabricating a plurality of different test structures on a wafer. Each of the plurality of test structures includes a first layer that is the thin film and a second layer that is a material under tensile stress. Step 554 includes inspecting the plurality of different test structures and step 556 includes identifying a subset of the plurality of different test structures. The subset of the plurality of different test structures may include all the broken test structures. Based on the identified subset, step 558 includes determining the tensile strength of the thin film.

According to further embodiments, method 550 may be modified to include only a single test structure. In such embodiments, the structure may be monitored for a known or specific fracture strength. In some embodiments, two test structures may be used in order to establish a known upper and lower bound for fracture strength. In still further embodiments, fractured and non-fractured test structures may be used in electrical tests as well. In such embodiments, each test structure may include a conductive material coupled to metallization or contact pads, for example. Electrical signals may be applied to the conductive material across the beam forming the test structure. Fractured test structures exhibit open circuit characteristics and non-fractured test structures exhibit short circuit characteristics, which may provide useful electrical properties during test.

According to various embodiments, method 550 may include further steps and further tests. All the test structures described herein and equivalents may be included in the plurality of different test structures and numerous test groups may be selected in order to determine the tensile strength of the thin film. Further, multiple thin films of layers may be tested on a wafer by fabricating multiple test structures associated with different thin films or layers.

According to various embodiments, a micro-fabricated test structure includes a structure mechanically coupled between two rigid anchors and disposed above a substrate. The structure is released from the substrate and includes a test layer mechanically coupled between the two rigid anchors. The test layer includes a first region having a first cross-sectional area and a constricted region having a second cross-sectional area smaller than the first cross-sectional area. The structure also includes a first tensile stressed layer disposed on a surface of the test layer adjacent the first region.

In various embodiments, a width of the constricted region is tapered from a widest point to a narrowest point. A width of the constricted region may also be constant. The test layer may have a hole that forms the constricted region next to the hole. The test structure may also include an electrode disposed on the substrate below the structure. In some embodiments, the test structure includes a second tensile stressed layer disposed on a bottom surface of the test layer below the first region. The first tensile stressed layer may be disposed on a top surface of the test layer above the first region. In an embodiment, the second cross-sectional area is less than 50% of the first cross-sectional area. The first tensile stressed layer may be configured to apply a tensile stress to the test layer that is not operable to cause the test layer to fracture.

According to various embodiments, a micro-fabricated test structure includes a plurality of tensile stress structures fabricated on a wafer. Each of the plurality of tensile stress structures includes a test layer with a first portion and a second portion and a first tensile stress layer disposed on the first portion of the test layer and not on the second portion of the test layer. The second portion of the test layer includes a constricted region having a cross-sectional area smaller than the first portion of the test layer. A first tensile stress structure of the plurality of tensile stress structures has a first test dimension and a second tensile stress structure of the plurality of tensile stress structures has a second test dimension. The second test dimension is different from the first test dimension.

In various embodiments, the test dimension includes a planar area of the first portion of the test layer, a width of the test layer at a center of the constricted region, a length of the constricted region, or a planar area of a cutout region in the second portion of the test layer. The cutout region may include a region where the test layer is removed forming a hole in the test layer. In some embodiments, the cutout region has a rectangular shape, the cutout region has a circular shape, or the cutout region includes two holes in the test layer. The test dimension may vary from a first value for the first tensile stress structure to a second value for a last tensile stress structure.

In various embodiments, each of the plurality of tensile stress structures also includes a second tensile stress layer disposed on a surface of the test layer opposite the first tensile stress layer and on the first portion of the test layer and not on the second portion of the test layer. A first subset of the plurality of tensile stress structures may be configured to break during or after fabrication due to a tensile stress applied by the first tensile stress layer to the test layer and a second subset of the plurality of tensile stress structures may be configured not to break during fabrication. The test layer may form a beam between two rigid anchors and the beam has a constant width throughout an entire length of the beam. In other embodiments, the test layer forms a beam between two rigid anchors and the beam has a tapered width throughout a length of the beam such that the width is narrowest in the constricted region.

According to various embodiments, a micro-fabricated test structure includes a plurality of tensile stress structures fabricated on a wafer. Each of the plurality of tensile stress structures includes a test layer comprising a first portion and a second portion and a tensile stress layer disposed on the first portion of the test layer and not on the second portion of the test layer. The second portion of the test layer includes a constricted region having a cross-sectional area smaller than the first portion of the test layer. The plurality of tensile stress structures include tensile stress structures having tensile stress layers configured to apply different tensile stress densities to the test layer on which the respective tensile stress layer is disposed.

In various embodiments, a first subset of the plurality of tensile stress structures is configured to break during fabrication and a second subset of the plurality of tensile stress structures is not configured to break during fabrication. The first and second subsets indicate a tensile strength of the test layer. In some embodiments, the test layer forms a beam between two rigid anchors and the beam has a tapered width throughout a length of the beam such that the width is narrowest in the constricted region. In other embodiments, the beam has a constant width throughout an entire length of the beam and the constricted region comprises hole in the test layer. The plurality of tensile stress structures are may be configured with different sized constricted regions such that some constricted regions will fracture at a lower tensile stress.

According to various embodiments, a method of determining a tensile strength of a thin film includes fabricating a plurality of different test structures on a wafer, inspecting the plurality of different test structures, identifying a subset of the plurality of different test structures based on the inspecting, and determining the tensile strength of the thin film based on the identified subset. Each of the plurality of test structures includes a first layer including the thin film and a second layer with a material under tensile stress. The subset includes broken test structures.

In various embodiments, the plurality of different test structures includes structures under different tensile stresses. Each of the plurality of different test structures may include a constricted region of the first layer.

According to various embodiments, a method of fabricating a test structure includes disposing a sacrificial material on a substrate, disposing a thin film on the sacrificial material, disposing a first tensile stress material on the thin film, patterning the first tensile stress material to expose a portion of the thin film, patterning the thin film in the exposed portion to create a constricted region, and removing the sacrificial material to release the test structure.

In various embodiments, the method also includes disposing a second tensile stress material below the thin film and patterning the second tensile stress material. The tensile stress material may include silicon nitride. The thin film may include polysilicon. In some embodiments, the method also includes forming an electrode on the substrate below the thin film. The method may also include forming a plurality of test structures having different values of a test dimension. In some embodiments, the test dimension is related to a tensile stress applied to the thin film of each of the plurality of test structures and the different values correspond to different tensile stresses applied to the thin film of each of the plurality of test structures. In other embodiments, the test dimension is related to a cross-sectional area of a constricted region formed in the thin film of each of the plurality of test structures and the cross-sectional area of the constricted region corresponds to a fracture strength of the test structure.

Advantages of the various embodiments described herein may include a test structure that is easily used to determine the fracture strength or tensile strength of a thin film in a fabricated device. In some embodiments, the test structure may be used to determine the fracture strength without the use of specialized test equipment. Particularly, the test structure may be combined with optical inspection through a microscope. A further advantage includes a test structure that is highly compatible with IC or MEMS fabrication sequences and causes little or no impact on a fabrication sequence. According to a further advantage, test structures described herein may also be incorporated in an electrical test by applying an electrical signal to both fractured and non-fractured test structures including a conductive material. In such embodiments, the fractured test structures exhibit open circuit characteristics and the non-fractured test structures exhibit short circuit characteristics.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A micro-fabricated test structure comprising:
a structure mechanically coupled between two rigid anchors and disposed above a substrate, wherein the structure is released from the substrate, the structure comprising:
a test layer having a first end attached to a first one of the two rigid anchors and a second end attached to a second one of the two rigid anchors, wherein the test layer comprises a first region adjacent to each of the two rigid anchors and having a first cross-sectional area, and wherein the test layer further comprises a constricted region having a second cross-sectional area smaller than the first cross-sectional area; and
a first tensile stressed layer separate from the test layer, the first tensile stressed layer disposed on a surface of the test layer adjacent the first region.

2. The test structure of claim 1, wherein a width of the constricted region is tapered from a widest point to a narrowest point.

3. The test structure of claim 1, wherein a width of the constricted region is constant.

4. The test structure of claim 1, wherein the test layer has a hole that forms the constricted region next to the hole.

5. The test structure of claim 1, further comprising an electrode disposed on the substrate below the structure.

6. The test structure of claim 1, further comprising a second tensile stressed layer disposed on a bottom surface of the test layer below the first region, and wherein the first tensile stressed layer is disposed on a top surface of the test layer above the first region.

7. The test structure of claim 1, wherein the second cross-sectional area is less than 50% of the first cross-sectional area.

8. The test structure of claim 1, wherein the first tensile stressed layer is configured to apply a tensile stress to the test layer, and wherein the tensile stress is not operable to cause the test layer to fracture.

9. A micro-fabricated test structure comprising:
a plurality of tensile stress structures fabricated on a wafer, wherein:

each of the plurality of tensile stress structures comprises:
- a test layer comprising a first portion and a second portion, wherein the second portion of the test layer comprises a constricted region having a cross-sectional area smaller than the first portion of the test layer, and
- a first tensile stress layer disposed on the first portion of the test layer and not on the second portion of the test layer;
- a first plurality of tensile stress structures of the plurality of tensile stress structures has a constant first test dimension and a varying second test dimension; and
- a second plurality of tensile stress structures of the plurality of tensile stress structures has a constant second test dimension and a varying first test dimension, the second test dimension being different from the first test dimension.

10. The test structure of claim 9, wherein the first test dimension comprises a planar area of the first portion of the test layer.

11. The test structure of claim 9, wherein the second test dimension comprises a width of the test layer at a center of the constricted region.

12. The test structure of claim 9, wherein the second test dimension comprises a length of the constricted region.

13. The test structure of claim 9, wherein the second test dimension comprises a planar area of a cutout region in the second portion of the test layer, wherein the cutout region comprises a region where the test layer is removed forming a hole in the test layer.

14. The test structure of claim 13, wherein the cutout region has a rectangular shape.

15. The test structure of claim 13, wherein the cutout region has a circular shape.

16. The test structure of claim 13, wherein the cutout region comprises two holes in the test layer.

17. The test structure of claim 9, wherein each of the plurality of tensile stress structures further comprises a second tensile stress layer disposed on a surface of the test layer opposite the first tensile stress layer and on the first portion of the test layer and not on the second portion of the test layer.

18. The test structure of claim 9, wherein a first subset of the plurality of tensile stress structures are configured to break during or after fabrication due to a tensile stress applied by the first tensile stress layer to the test layer and a second subset of the plurality of tensile stress structures are configured not to break during fabrication.

19. The test structure of claim 9, wherein the test layer forms a beam between two rigid anchors and the beam has a constant width throughout an entire length of the beam.

20. The test structure of claim 9, wherein the test layer forms a beam between two rigid anchors and the beam has a tapered width throughout a length of the beam such that the width is narrowest in the constricted region.

21. A micro-fabricated test structure comprising:
a plurality of tensile stress structures fabricated on a wafer, wherein:
  each of the plurality of tensile stress structures comprises:
    a test layer comprising a first portion and a second portion, wherein the second portion of the test layer comprises a constricted region having a cross-sectional area smaller than the first portion of the test layer, and
    a first tensile stress layer disposed on the first portion of the test layer and not on the second portion of the test layer;
    a second tensile stress layer disposed on a surface of the first portion of the test layer opposite the first tensile stress layer and not on the second portion of the test layer; and
  the plurality of tensile stress structures comprise tensile stress structures having the first tensile stress layer and the second tensile stress layer configured to apply different tensile stress densities to the test layer on which the respective first tensile stress layer and second tensile stress layer are disposed.

22. The test structure of claim 21, wherein a first subset of the plurality of tensile stress structures is configured to break during fabrication and a second subset of the plurality of tensile stress structures is not configured to break during fabrication, wherein the first and second subsets indicate a tensile strength of the test layer.

23. The test structure of claim 22, wherein the test layer forms a beam between two rigid anchors and the beam has a tapered width throughout a length of the beam such that the width is narrowest in the constricted region.

24. The test structure of claim 22, wherein the test layer forms a beam between two rigid anchors, the beam has a constant width throughout an entire length of the beam, and the constricted region comprises hole in the test layer.

25. The test structure of claim 22, wherein the plurality of tensile stress structures are configured with different sized constricted regions such that some constricted regions will fracture at a lower tensile stress.

* * * * *